United States Patent [19]

Rosenberger

Best Available Copy

[11] E Re. 30,260

[45] Reissued Apr. 22, 1980

[54] 1-(2,6,6-TRIMETHYL-3-HYDROXY-1-CYCLOHEXEN-1-YL)-3-METHYL-PENTA-1,4-DIENE[OR 1-YN-4-EN]-3-OLS

[75] Inventor: Michael Rosenberger, Caldwell, N.J.

[73] Assignee: Hoffmann-La Roche Inc., Nutley, N.J.

[21] Appl. No.: 16,868

[22] Filed: Mar. 2, 1979

Related U.S. Patent Documents

Reissue of:

[64] Patent No.: 4,098,827
Issued: Jul. 4, 1978
Appl. No.: 759,703
Filed: Jan. 17, 1977

[51] Int. Cl.[2] ..... C07C 35/18

[52] U.S. Cl. ..... 568/824; 260/348.55; 260/586 R; 260/586 C; 260/586 P; 260/590 C; 260/590 E

[58] Field of Search ..... 568/824

[56] References Cited

U.S. PATENT DOCUMENTS

| | | | |
|---|---|---|---|
| 2,726,269 | 12/1955 | Hamphlett | 568/824 |
| 2,819,298 | 1/1958 | Isler et al. | 568/824 |
| 3,932,485 | 1/1976 | Surmatis | 568/824 |
| 3,947,498 | 3/1976 | Oroshnik | 568/824 |
| 4,000,198 | 12/1976 | Rosenberger | 260/586 C |

FOREIGN PATENT DOCUMENTS 2037935 2/1971 Fed. Rep. of Germany .

*Primary Examiner*—Joseph E. Evans
*Attorney, Agent, or Firm*—Jon S. Saxe; Bernard S. Leon; William H. Epstein

[57] ABSTRACT

A total synthesis of canthaxanthin, a known food coloring agent from alpha or retro ionone.

1 Claim, No Drawings

1-(2,6,6-TRIMETHYL-3-HYDROXY-1-CYCLOHEX-EN-1-YL)-3-METHYL-PENTA-1,4-DIENE[OR 1-YN-4-EN]-3-OLS

Matter enclosed in heavy brackets [ ] appears in the original patent but forms no part of this reissue specification; matter printed in italics indicates the additions made by reissue.

CROSS REFERENCE TO RELATED APPLICATION

This application is related to Ser. No. 585,224, filed Jul. 9, 1975, Rosenberger et al. now U.S. Pat. No. 4,006,186.

SUMMARY OF INVENTION

In accordance with this invention, a method is provided for synthesizing canthaxanthin which has the formula;

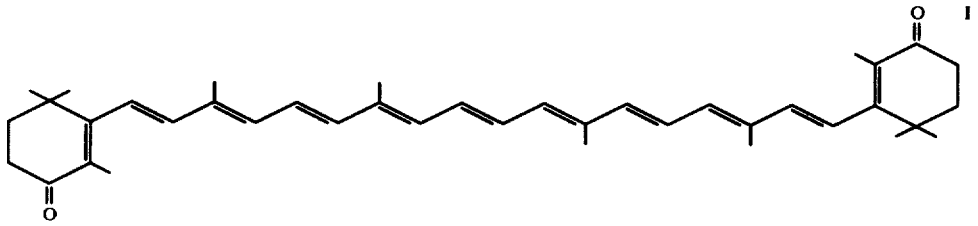

I from either α-ionone which has the formula

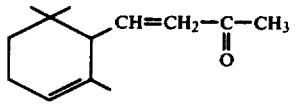

II or retroionone

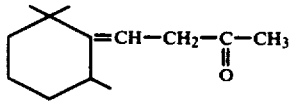

IIa

DETAILED DESCRIPTION

The term halogen as used throughout this specification includes all four halogens, i.e. chlorine, fluorine, bromine and iodine. The term "lower alkyl" as used herein designates a saturated aliphatic straight or branched chain hydrocarbon containing from 1 to 7 carbon atoms such as ethyl, methyl, isopropyl, etc. The term "lower alkoxy" as used throughout the specification denotes lower alkoxy groups containing from 1 to 7 carbon atoms such as methoxy, ethoxy, isopropoxy, etc.

As used herein, the term "aryl" designates mononuclear aromatic hydrocarbon groups such as phenyl, tolyl, which can be unsubstituted or substituted in one or more positions with a halogen, nitro, lower alkyl or lower alkoxy substituent and polynuclear aryl groups such as naphthyl, anthryl, phenanthryl, which can be unsubstituted or substituted with one or more of the aforementioned groups. The preferred aryl groups are the substituted and unsubstituted mononuclear groups, particularly phenyl. The term "alkali metal" includes all alkali metals such as sodium, potassium and lithium. The term "lower alkanol" designates aliphatic unsaturated alcohols containing from 1 to 7 carbon atoms such as methanol, ethanol, isopropanol, n-butanol etc.

In the first steps in the production of the compound of formula I in accordance with this invention, the compound of formula II is converted to a compound of formula

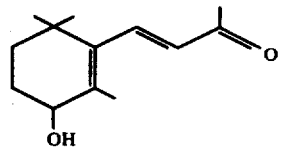

IV via the following intermediate:

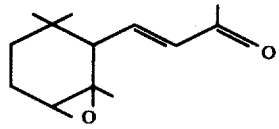

V

The compound of formula II is converted to the compound of formula V by reaction with a per-organic acid. In this procedure, any method of converting an unsaturated double bond to an epoxy bridge can be utilized. Among the preferred per-organic acids are included per-acetic acid, per-benzoic acid, m-chloroper-benzoic acid etc. Any conventional per-organic acid can be utilized for this purpose. Any of the conventional reaction conditions utilized in forming epoxides can be used in this reaction.

The compound of formula V is converted to the compound of formula IV by treatment with alklai metal lower alkoxide. Any conventional alklai metal lower alkoxide can be utilized such as sodium or potassium methoxide. This reaction is carried out in a lower alkanol solvent. Among the preferred solvents are methanol and ethanol. However, any conventional lower alkanol can be utilized. If desired, an inert organic solvent such as benzene, toluene, etc. can be used with the lower alkanol solvent. In this regard, any conventional inert organic solvent can, if desired, be incorporated in the lower alkanol solvent medium. In carrying out this reaction, temperature and pressure are not critical and this reaction can be carried out at room temperature and atmospheric pressure. On the other hand, any temperature of from 10° C. to 100° C. can be utilized in carrying out this reaction.

On the other hand, the compound of formula IV can be prepared from retroionone, i.e. a compound of formula II-a via the following intermediate:

VI

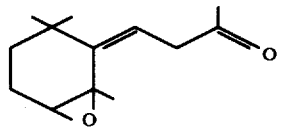

The compound of formula II-a is converted to the compound of formula VI by epoxidation via a perorganic acid in the manner described in connection with the reaction of a compound of formula II to a compound of formula V. The compound of formula VI is converted to the compound of the formula IV by treating the compound of formula VI with an alklai metal lower alkoxide in a lower alkanol solvent in the same manner as described in connection with the conversion of a compound of the formula V to a compound of formula IV.

The compound of formula IV is converted in the next series of steps to a phosphonium salt of the formula:

VIII

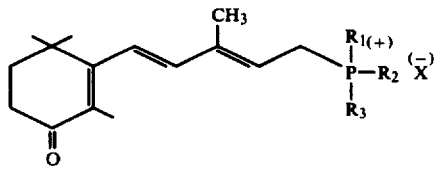

wherein $R_1$, $R_2$ and $R_3$ are aryl or lower alkyl; and X is halogen.

In this conversion, the following intermediates are formed

IX

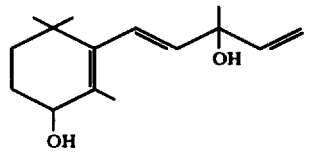

X

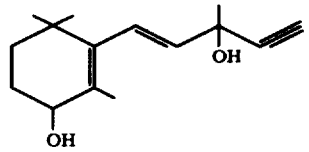

XI

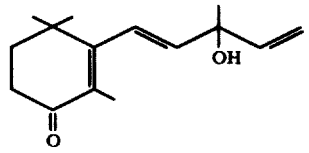

XII

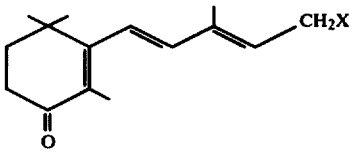

where X is as above.

In the conversion of a compound of formula IV to a compound of formula IX, the compound of formula IV is treated with a vinylmetalic halide such as vinyl magnesium chloride under conditions conventional for reacting a ketone with an organo metallic halide. In carrying out this reaction, it is generally preferred to utilize at least 2 moles of the vinyl metallic halide per mole of the compound of formula IV. If desired, the vinylmetalic halide can be utilized in amounts of 10 moles or more per mole of the compound of formula IV. However, no beneficial results are achieved by utilizing such large an amount of the vinyl magnesium halide. Furthermore, due to the cost of utilizing such large amounts, amounts of the vinyl metallic halide of greater than 10 moles per mole of the compound of formula IV are seldom utilized.

The compound of formula X can be prepared from the compound of formula IV by reacting the compound of formula IV with an alkali metal acetalide such as sodium acetalide. Any of the conditions conventional in reacting a ketone with an acetalide to form an addition product can be utilized in accordance with this invention. The compound of formula X can be converted to the compound of formula IX via hydrogenation utilizing a Lindlar catalyst. Any conventional method of selectively reducing a triple bond to a double bond can be utilized in carrying out this reaction.

The compound of formula IX is converted to the compound of formula XI by treatment with a oxidizing agent. Any conventional oxidizing agent can be utilized to affect this conversion. Among the preferred oxidizing agents are included maganese dioxide and the chromate oxidizing agents such as Jones reagent. Any of the conditions conventional in carrying out oxidation utilizing these reagents can be utilized in the conversion of a compound of formula X to a compound of formula XI.

Among the preferred methods for carrying out the conversion of a compound of formula X to a compound of formula XI is by oxidation with aluminum isopropoxide in the presence of acetone. It is through this method that the compound of formula XI is produced in high yields from the compound of formula X. In carrying out this reaction, the aluminum isopropoxide can be present in catalytic quantities, i.e. at least 0.1 mole percent based upon the moles of the compound of formula IX. If desired, the aluminum isopropoxide can be present in an amount of 100 mole percent based upon the compound of formula IX. In fact, any excess of the aluminum isopropoxide will not deleteriously affect this reaction. However, for economics it is generally preferred to utilize the aluminum isopropoxide in an amount of from 0.1 mole percent to 100 mole percent based upon the weight of the compound of formula IX.

Generally, the oxidation with aluminum isopropoxide and acetone can be carried out in the presence of an inert organic solvent such as methylene chloride, benzene and toluene. In fact, any inert organic solvent can, if desired, be utilized in a mixture with acetone. Generally, this reaction is carried out at the reflux temperature of the reaction medium.

The compound of formula XI is converted to the compound of formula XII by treating the compound of formula XI with a phosphorous trihalide. Generally, this reaction is carried out in an inert organic solvent. Any conventional inert organic solvent can be utilized to carry out this reaction. Among the preferred solvents are the ether solvents such as diethyl ether, tetrahydrofuran, etc. In carrying out this reaction, temperature and pressure are not critical and this reaction can be carried out at room temperature and atmospheric pressure. Generally it is preferred to carry out this reaction at a temperature of from 10° C. to 100° C.

The compound of formula XII is converted to the compound of formula X by reacting the compound of formula XII with a phosphine of the formula

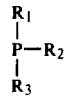

XIII wherein $R_1$, $R_2$ and $R_3$ are as above.

This reaction is generally carried out in an inert organic solvent. Any conventional inert organic solvent can be utilized to carry out this reaction. Among the preferred solvents are the ether solvents and the hydrocarbon solvents such as benzene, toluene, etc. In carrying out this reaction, temperature and pressure are not critical and generally this reaction can be carried out at room temperature and atmospheric pressure. Generally, it is preferred to carry out this reaction by heating the reaction medium to the reflux temperature.

In accordance with another embodiment of this invention, the compound of formula X can be directly prepared from the compound of formula XI by treating the compound of formula XI with the hydrohalic acid salt of the phosphine of formula XIII. Among the hydrohalic acid salts, triphenylphosphine hydrobromide is preferred. This reaction is generally carried out in a inert organic solvent. Any conventional inert organic solvent can be utilized for this purpose. Among the preferred solvents are included the halogenated hydrocarbon solvents such as dichloromethane, methylene, chloride, etc. In carrying out this reaction, temperature and pressure are not critical and this reaction can be carried out at room temperature and atmospheric pressure. If desired, higher or lower temperatures can be utilized.

The compound of formula I is formed from the compound of formula X by reacting the compound of formula X with a compound of the formula:

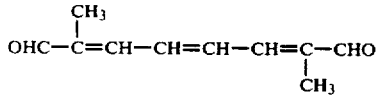

XX via a Wittig reaction.

This reaction is carried out utilizing conditions that are conventional in Wittig type reactions. In this reaction, two moles of the compound of formula X are reacted per mole of the compound of formula XX.

The invention will be more fully understood from the specific examples which follow. These examples are intended to illustrate the invention and are not to be construed as limitative thereof. In the Examples, the temperatures utilized are in degrees centigrade. When a mixture of organic liquids are utilized, the ratios set forth in the Examples is a volume ratio unless indicated otherwise.

EXAMPLE 1

4-(2,6,6-Trimethyl-2,3-epoxy-cyclohex-1-yl)-3-buten-2-one

A solution of m-chloro perbenzoic acid (23 g; 133 mol) in dichloromethane (200 ml) was cooled to 10° and treated with α-ionone (20.8 g; 92% purity) with cooling. After the complete addition, the mixture was stirred a further 20 min at room temperature (RT) and then cooled to 10° (t.l.c. analysis showed no α-ionone; 3:1 benzene/ethylacetate system).

To the cooled solution was added an aqueous solution of sodium hydroxide (100 ml; 2N) and the phases were then separated and the organic layer was washed with more base (100 ml; 2N), brine and dried over magnesium sulfate ($MgSO_4$).

Removal of the solids and distillation of the filtrate yielded pure 4-(2,6,6-Trimethyl-2,3-epoxy-cyclohex-1-yl)-3-buten-2-one (19.51 g); bp 113°–120° (0.5 mm) (4 inch vacuum jacketed vigreaux column).

EXAMPLE 2

Oxidation of α-ionone with peracetic acid

A mixture of peracetic acid (40%; 54G), anhydrous sodium acetate (10g) and dichloromethane (200 ml) was treated at RT with α-ionone (30 g; 94% purity) and the temperature was kept at RT with ice cooling. After the exotherm had subsided, the reaction mixture was stirred for a further 2 hours, treated with benzene (300 ml) and washed with a aqueous sodium bicarbonate solution (saturated), aqueous potassium metabisulfite and dried over $MgSO_4$.

Removal of the solids and concentrations to dryness yielded a 100% material balance of excellent quality 4-(2,6,6-Trimethyl-2,3-epoxy-cyclohex-1-yl)-3-buten-2-one (by pmr analysis).

EXAMPLE 3

(2,6,6-Trimethyl-3-hydroxy-1-cyclohexen-1-yl)-3-oxo-trans-1-butene

The α-ionone epoxide 4-(2,6,6-Trimethyl-2,3-epoxycyclohex-1-yl)-3-buten-2-one (10 g) was dissolved in methanol, treated with a solution of sodium methoxide in methanol (1.41 Molar; 5ml) and heated at reflux for 2 hours (tlc, 3:1 benzene/ethylacetate, showed virtually complete conversion to product). After cooling to RT, diethyl ether (300 ml) was added and the mixture was washed with water and concentrated to dryness to yield the crude product (9g). This material was distilled through a short vigreaux column (3cm) to yield pure (2,6,6-Trimethyl-3-hydroxy-1-cyclohexen-1-yl)-3-oxo-trans-1-butene (5.95 g) bp 130°–140° (0.2–0.5 mm).

EXAMPLE 4

1-(2,6,6-Trimethyl-3-hydroxy-1-cyclohexene-1-yl)-3-methyl-penta-1,4-dien-3-ol A solution of vinylmagnesium chloride in tetrahydrofuran (THF; 190 ml; 2.3 Molar) was cooled to 0° and treated with a solution of the hydroxyketone, 4-(2,6,6-trimethyl-3-hydroxy-1-cyclohexen-1-yl)-3-oxo-trans-1-butene (17 g; distilled material) dissolved in THF (150 ml). After complete addition the reaction mixture was stirred an additional 1 hour at RT and then quenched with an aqueous solution of ammonium chloride (10% by weight; 200 ml).

Extraction with diethyl ether and concentration yielded the crude diol, 1-(2,6,6-trimethyl-3-hydroxy-1-cyclohexene-1-yl)-3-methyl-penta-1,4-diene-3-ol (30 g) as a thick oil.

A sample of this material (1g) was chromatographed on silica gel (100g) and yielded analytically pure 1-(2,6,6-trimethyl-3-hydroxy-1-cyclohexene-1-yl)-methyl-penta-1,4-diene-3-ol on elution with an ethylacetate-benzene mixture (1:1).

EXAMPLE 5

1-(2,6,6-Trimethyl-3-oxo-1-cyclohexen-1-yl)-3-methyl-penta-1,4-dien-3-ol

The crude diol 1-(2,6,6-Trimethyl-3-hydroxy-1-cyclohexene-1-yl)-3-methyl-penta-1,4-diene-3-ol (25 g) was dissolved in a mixture of dichloromethane (250 ml) and acetone (250 ml) and then heated at reflux for 16 hours with aluminum isopropoxide (50 g).

After cooling to RT the mixture was washed with dilute aqueous sulfuric acid (1N) and dried over $MgSO_4$.

Removal of the solids and solvents yielded the 1-(2,6,6-Trimethyl-3-oxo-1-cyclohexen-1-yl)-3-methyl-penta-1,4-dien-3-ol as a crude product (30 g).

Chromatography on silica gel (27g product on 400g) yielded the ketoalcohol 1-(2,6,6-Trimethyl-3-oxo-1-cyclohexen-1-yl)-3-methyl-penta-1,4-dien-3-ol (9.8g) on elution with an ether/hexane mixture (80%).

EXAMPLE 6

Phosphonium Salt

The hydroxyketone 1-(2,6,6-Trimethyl-3-oxo-1-cyclohexen-1-yl)-3-methyl-penta-1,4-dien-3-ol (4g) dissolved in diethyl ether (40 ml) was cooled to −20° and treated with a solution of phosphorous tribromide in diethyl ether (1 mole. equiv $PBr_3$; 80ml) and then warmed to RT. After stirring a further 1 hour at RT (while tlc indicated the rapid disappearance of starting material the yields of bromide were low if the reaction is worked up too soon) the mixture was cooled to 5° and carefully quenched with water (100 ml) and extracted with more ether.

The combined ether extracts were washed with saturated aqueous sodium bicarbonate solution, brine and dried over $MgSO_4$. Removal of the solids and concentration in vacuo yielded the 1-(2,6,6-Trimethyl-3-oxo-1-cyclohexen-1-yl)-3-methyl-5-bromo-penta-1,3-diene (4.15g).

EXAMPLE 7

The bromide of Example 6 was added to triphenylphosphine (4.4g) in benzene (30 ml) and heated at reflux for 1 hour. The mixture was then cooled to RT treated with diethyl ether (50 ml) and filtered to yield the 5-(2,6,6-trimethyl-3-oxo-cyclohexen-1-yl)-3-methyl-2,3-pentadiene-1-triphenylphosphonium bromide as a white powder (6.6g).

EXAMPLE 8

Retro-ionone (1.9g) was added to a solution of m-chloroperbenzoic acid (2.2g) dissolved in dichloromethane. This resulted in an exothermic reaction (~40°). After cooling, the mixture was washed with an aqueous sodium carbonate solution dried over $MgSO_4$ and taken to dryness to yield the epoxide, the 1-(2,6,6-Trimethyl-2,3-epoxy-1-cyclohexylidene)-buten-2-one. This epoxide (~2g) was dissolved in a solution of methanolic sodium methoxide (1.4 Molar; 20ml) and left at RT for ½ hour (instant color change and probably complete reaction). Dilution with ether followed by a brine washing yielded 1-(2,6,6,-trimethyl-3-hydroxy-1-cyclohexen-1-yl)-3-oxo-1-butene, upon chromatography over silica gel.

EXAMPLE 9

1-(2,6,6-Trimethyl-3-oxo-1-cyclohexen-1-yl)-3-methyl-penta-1,4-dien-3-ol

A solution of α-ionone (202.5g; 94% by glc) in dichloromethane (1100 ml) containing anhydrous sodium acetate (50g) was cooled to 15° and treated over 30 min with peracetic acid (250 ml; 40% in acetic acid; from FMC).

After stirring for 2½ hours the reaction was no longer exothermic and the reaction mixture was stirred a further 3 hours at RT and then washed with water (2×500 ml), aqueous potassium metabisulfite solution (10%; 2×250 ml), sodium hydroxide solution (2 M; 400ml) and water (400ml). Removal of the solvents gave the 4-(2,6,6-trimethyl-2,3-epoxy-cyclohex-1-yl)-3-buten-2-one having a nmr spectrum virtually identical with a distilled sample.

This material was dissolved in methanol (800ml), treated with a methanolic solution of sodium methoxide (100ml; 1.4M) and heated at reflux for 3 hours (tlc; 1:1 benzene/ethylacetate). After cooling to RT acetic acid (9ml) was added, followed by water (180ml) and the mixture was then extracted with hexane saturated with an 80% methanol/water mixture (500 & 2×250ml). The hexane extracts were back extracted with an 80% methanol/water mixture (saturated with hexane) and the combined methanolic extracts were concentrated and re-extracted into ether. Removal of the ether gave the desired hydroxyketone 4-(2,2,6-Trimethyl-3-hydroxy-1-cyclohexen-1-yl)-3-oxo-trans-1-butene; (204.1g) as an oil.

This crude product was dissolved in tetrahydrofuran THF; 1000 ml) cooled to −30° and then treated with a freshly prepared solution of vinylmagnesium chloride (680ml; 3.3M) in THF. The first portion (350ml) was added between −30° and −10° followed by the remainder at −10°→0°. At this stage the mixture is difficult to stir and after a further 30 min at 10° diethyl ether (1000 ml) was added (to help the stirring) followed by a saturated solution of ammonium chloride (250ml). The solids were filtered off, washed well with more ether and the combined filtrates were concentrated to yield the diol, 1-(2,6,6-Trimethyl-3-hydroxy-1-cyclohexene-1-yl)-3-methyl-penta-1,4-diene-3-ol (231.8g).

This crude diol (216.9g) in a mixture of acetone and dichloromethane (1:1; 2000ml) containing aluminum isopropoxide (400g) was heated at reflux for 5 hours (tlc; 1:1 benzene/ethyl acetate), cooled, treated with more dichloromethane (1000ml) and then acidified with aqueous sulfuric acid (2N; 2000ml) with ice cooling. The aqueous layer was back-washed with more dichloromethane (4×500ml) and the combined extracts were then concentrated to ca 600ml, dried over magnesium sulfate and then taken to dryness to yield a crude hydroxyketone, 1-(2,6,6-trimethyl-3-oxo-1-cyclohexen-1-yl)-3-methyl-penta-1,4-dien-3-ol (219.5g).

EXAMPLE 10

Phosphonium Salt

The hydroxyketone 1-(2,6,6-Trimethyl-3-oxo-1-cyclohexene-1-yl)-3-methyl-penta-1,4-diene-3-ol (136.6 g) was dissolved in diethyl ether (1000ml) cooled to −20° and exposed to a solution of phosphorous tribromide (50ml) in ether (250ml) and then stirred for 1 hour at RT. After this period, the mixture was cooled to 5°, treated with water (500 ml; care) and the ether layer was then washed well with water, saturated aqueous sodium bicarbonate solution, brine and then dried over anhydrous magnesium sulfate. (All the aqueous extracts were back-washed with more diethyl ether.)

Removal of the solvents yielded the crude bromide (147g) 1-(2,6,6-Trimethyl-3-oxo-1-cyclohexene-1-yl)-3-methyl-5-bromo-penta-1,3-diene, which was dissolved in benzene (1000ml) containing triphenylphosphine (144g) and heated at reflux for 1½ hours. The mixture, was then cooled to RT, treated with diethyl ether (1000 ml) and stirred for ca 1 hour (the thick syrup slowly yields a granular product).

The solids were filtered off and washed with more diethyl ether and dried to yield the crude salt (296.7g) which was a mixture of at least two salts (tlc; n-butyl acetate/formic acid/water; 80:18:2). This material (269.3g) was dissolved in dichloromethane (2500ml) and treated with diethyl ether (125ml) and filtered. The filtrate was concentrated to dryness to yield 5-(2,6,6-Trimethyl-3-oxo-cyclohexen-1-yl)-2-methyl-2,3-pentadiene-1-triphenylphonium bromide (38.5g) mp 261°-63°.

EXAMPLE 11

The hydroxyketone 1-(2,6,6-Trimethyl-3-hydroxy-1-cyclohexene-1-yl)-3-methyl-penta-1,4-diene-3-ol (10.7 g) dissolved in dichloromethane (25ml) was treated with triphenylphosphine hydrobromide (14.4g; 0.9mol equiv) in more dichloromethane (50ml) and left overnight at RT (the reaction is exothermic and complete in ca 1 hours). Most of the solvents were then evaporated off and thick syrupy residue was digested with diethyl ether and filtered. The residue was then dried to give 5-(2,6,6-Trimethyl-3-oxo-cyclohexen-1-yl)-3-methyl-2,4-pentadiene-1-triphenylphosphonium bromide as solid (23.5g) which assayed for ca 84% pure by nmr analysis.

EXAMPLE 12

Canthaxanthin

A solution of the pure trans dialdehyde-2,7-dimethyl-2,4,6-octatriene-1,8-dial (1.64g) and the phosphonium salt, 5-(2,6,6-Trimethyl-3-oxo-cyclohexen-1-yl)-3-methyl-2,4-pentadiene-1-triphenylphosphonium bromide (14.6g) in dichloromethane (50ml) was cooled to −10° and treated over 15 min with a methanolic solution of sodium methoxide (3.6Molar; 6.7ml) and then stirred a further 30 min at −10°→−5°.

After this time the mixture was washed with water and the solvents were removed to give the crude product and triphenylphosphine oxide (14.5g). This material was chromatographed on silica gel (200g) to yield the carotenoid fraction (6.47g) on elution with benzene/ethyl acetate mixtures (tlc; 10% ether/dichloromethane). Crystallization from dichloromethane/methanol gave canthaxanthin (2.76g). The mother liquors were concentrated to dryness, dissolved in hot isopropanol and cooled to RT. Filtering of the solvents gave a further amount of canthaxanthin (0.91 g). The filtrate from this crystallization was concentrated and the residue was then heated at reflux in water (100ml) for 18 hours. Crystallization of the residue from a dichloromethane/methanol mixture gave a further quantity of canthaxanthin (1.02g).

I claim:

[1. A compound of the formula:

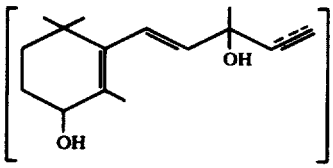

where the dotted bond is hydrogenated.]

[2. The compound of claim 1 wherein said compound is 1-(2,6,6-trimethyl-3-hydroxy-1-cyclohexen-1-yl)-3-methyl-penta-1,4-diene-3-ol.]

*3. A compound of the formula:*

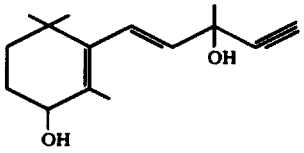

* * * * *